United States Patent
Kuo

(10) Patent No.: US 11,931,392 B2
(45) Date of Patent: Mar. 19, 2024

(54) USE OF MAGNOLIA FIGO EXTRACT IN THE MANUFACTURE OF COMPOUND FOR INHIBITING GROWTH OF LUNG CANCER CELLS

(71) Applicant: Chun-Sheng Kuo, Taichung (TW)

(72) Inventor: Chun-Sheng Kuo, Taichung (TW)

(73) Assignee: Chun-Sheng Kuo, Taichung (TW)

( * ) Notice: Subject to any disclaimer, the term of this patent is extended or adjusted under 35 U.S.C. 154(b) by 79 days.

(21) Appl. No.: 17/394,047

(22) Filed: Aug. 4, 2021

(65) Prior Publication Data

US 2022/0401504 A1 Dec. 22, 2022

(30) Foreign Application Priority Data

Jun. 18, 2021 (TW) .................. 110122264

(51) Int. Cl.
| | | |
|---|---|---|
| *A61K 36/575* | (2006.01) | |
| *A61K 31/015* | (2006.01) | |
| *A61K 31/045* | (2006.01) | |
| *A61K 31/232* | (2006.01) | |
| *A61P 35/00* | (2006.01) | |

(52) U.S. Cl.
CPC .......... *A61K 36/575* (2013.01); *A61K 31/015* (2013.01); *A61K 31/045* (2013.01); *A61K 31/232* (2013.01); *A61P 35/00* (2018.01)

(58) Field of Classification Search
None
See application file for complete search history.

(56) References Cited

PUBLICATIONS

Zhai et al (Int J Nanomedicine 13:6279-6296, 2018) (Year: 2018).*
Toda et al (J Agric Food Chem 30:81-84, 1982) (Year: 1982).*
Accession No. 2008:811078 containing CAS RN 7212-44-4 (English language abstract of Wang et al (Jingxi Huagong 24(5):477-479, 2007) (Year: 2007).*
Accession No. 2008:811078 containing CAS RN 59149-01-8 (English language abstract of Wang et al (Jingxi Huagong 24(5):477-479, 2007) (Year: 2007).*
Kuo et al (Molecules 28:7445, 2023) (Year: 2023).*
Zou et al (Clinics 70:556-562, 2015) (Year: 2015).*

* cited by examiner

*Primary Examiner* — Craig D Ricci

(57) ABSTRACT

A use of *Magnolia figo* extract in the manufacture of a compound for inhibiting growth of lung cancer cells.

10 Claims, 4 Drawing Sheets

USE OF MAGNOLIA FIGO EXTRACT IN THE MANUFACTURE OF COMPOUND FOR INHIBITING GROWTH OF LUNG CANCER CELLS

FIELD OF THE INVENTION

The present invention relates to a use of *Magnolia figo* extract, and more particularly relates to a use of *Magnolia figo* extract in the manufacture of a compound for inhibiting growth of lung cancer cells.

BACKGROUND OF THE INVENTION

Lung cancer is a malignant tumor that grows in the bronchi or alveoli. In recent years, the number of lung cancer patients all over the world has not only increased significantly, but lung cancer has been with the highest cancer mortality rate for many years.

The treatment of lung cancer is complex and ever-improving day by day, which could be seen in many kinds of treatment including surgery, chemotherapy, radiation therapy, targeted therapy and immunotherapy. However, the conventional treatments are expensive. Moreover after long-term use of drugs, body resistance and more or less side effects happens to patients, which may increase the physical burden for patients.

Therefore, the conventional methods for inhibiting the growth of the lung cancer cells in prior art still need to be improved.

SUMMARY OF THE INVENTION

Therefore, one objective of the present invention is to provide a use of *Magnolia figo* extract in the manufacture of a compound for inhibiting growth of lung cancer cells, which can inhibit, in a purely natural manner, the growth of the lung cancer cells, thereby reducing the physiological and economic burden of patients.

In order to overcome the technical problems in prior art, the present invention provides a use of *Magnolia figo* extract in the manufacture of a compound for inhibiting growth of lung cancer cells.

In one embodiment of the present invention, the use of *Magnolia figo* extract in the manufacture of the compound for inhibiting growth of lung cancer cells is provided, wherein the compound is for facilitating apoptosis of the lung cancer cells.

In one embodiment of the present invention, the use of *Magnolia figo* extract in the manufacture of the compound for inhibiting growth of lung cancer cells is provided, wherein the *Magnolia figo* extract is *Magnolia figo* essential oil extract with a concentration range of 1 to 20 μg/ml.

In one embodiment of the present invention, the use of *Magnolia figo* extract in the manufacture of the compound for inhibiting growth of lung cancer cells is provided, wherein the *Magnolia figo* essential oil extract is prepared by the following steps: a pre-treatment step of washing and breaking *Magnolia figo*; and an extraction step of performing a supercritical fluid extraction on a product obtained in the pre-treatment step to obtain the *Magnolia figo* essential oil extract.

In one embodiment of the present invention, the use of *Magnolia figo* extract in the manufacture of the compound for inhibiting growth of lung cancer cells is provided, wherein the compound further contains a compound carrier, an excipient, or the combinations thereof.

In one embodiment of the present invention, the use of *Magnolia figo* extract in the manufacture of the compound for inhibiting growth of lung cancer cells is provided, wherein the *Magnolia figo* extract contains sesquiterpene, sesquiterpenol, monoterpenol, and ester.

In one embodiment of the present invention, the use of *Magnolia figo* extract in the manufacture of the compound for inhibiting growth of lung cancer cells is provided, wherein the sesquiterpene contained in the *Magnolia figo* extract is one or more selected from α-cubebene, α-copaene, β-cubebene, β-elemene, β-caryophyllene, γ-elemene, α-humulene, germacrene D, β-selinene, α-selinene, δ-cadinene, germacrene B, and β-caryophyllene oxide.

In one embodiment of the present invention, the use of *Magnolia figo* extract in the manufacture of the compound for inhibiting growth of lung cancer cells is provided, wherein the sesquiterpenol contained in the *Magnolia figo* extract is nerolidol.

In one embodiment of the present invention, the use of *Magnolia figo* extract in the manufacture of the compound for inhibiting growth of lung cancer cells is provided, wherein the monoterpenol contained in the *Magnolia figo* extract is linalool.

In one embodiment of the present invention, the use of *Magnolia figo* extract in the manufacture of the compound for inhibiting growth of lung cancer cells is provided, wherein the ester contained in the *Magnolia figo* extract is methyl(Z)-5,11,14,17-eicosatetraenoate.

By way of the technical means adopted by the present invention, the compound can effectively inhibit, in a purely natural manner, growth of lung cancer cells and thereby reduce the physiological and economic burden of patients with lung cancer.

DETAILED DESCRIPTION OF THE PREFERRED EMBODIMENTS

Figure 1A:
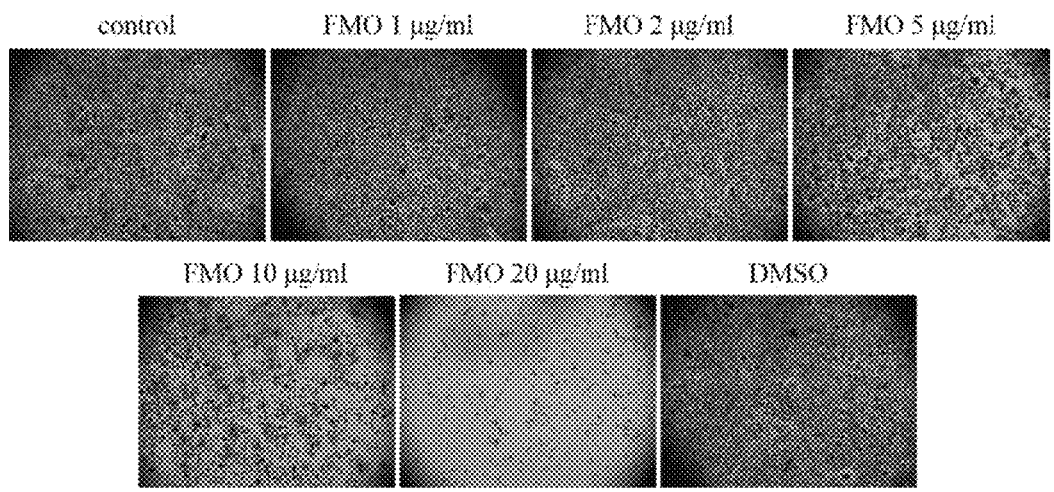
FIG. 1*a* is a drawing showing cell images from MTT assay according to an embodiment of the present invention.

The preferred embodiments of the present invention are described in detail below with reference to FIG. 1*a* to FIG. 3*c*. The description is used for explaining the embodiments of the present invention only, but not for limiting the scope of the claims.

As shown in FIGS. 1*a* to 3*c*, in an embodiment of the present invention, a use of *Magnolia figo* extract in the manufacture of a compound for inhibiting growth of lung cancer cells is provided, wherein the *Magnolia figo* extract is *Magnolia figo* essential oil extract with a concentration range of 1 to 20 µg/ml.

In detail, the concentrations of the *Magnolia figo* essential oil extracts used in the embodiment of the present invention are 1, 2, 5, 10, and 20 µg/ml, respectively.

Furthermore, the *Magnolia figo* essential oil extract is prepared by the following steps: a pre-treatment step of washing and breaking *Magnolia figo*; and an extraction step of performing a supercritical fluid extraction on a product obtained in the pre-treatment step to obtain the *Magnolia figo* essential oil extract.

Certainly, the extraction step of the *Magnolia figo* essential oil extract of the present invention is not limited to the method performed by using the supercritical fluid extraction. The *Magnolia figo* essential oil extract of the present invention can also be obtained by the extraction step using distillation, solvent extraction, or any method capable of extracting essential oils.

In detail, the *Magnolia figo* extract used in various assays performed in the embodiment of the present invention is the *Magnolia figo* essential oil extract (also referred to as the flower of *Magnolia* figo, "FMO") of the *Magnolia figo* extract with the highest efficacy obtained by the supercritical fluid extraction.

In the embodiment of the present invention, the use of *Magnolia figo* extract in the manufacture of the compound for inhibiting growth of lung cancer cells is provided, wherein the compound further contains a compound carrier and/or an excipient.

In the embodiment of the present invention, the use of *Magnolia figo* extract in the manufacture of the compound for inhibiting growth of lung cancer cells is provided, wherein the *Magnolia figo* extract contains sesquiterpene, sesquiterpenol, monoterpenol, and ester.

In the embodiment of the present invention, the use of *Magnolia figo* extract in the manufacture of the compound for inhibiting growth of lung cancer cells is provided, wherein the sesquiterpene contained in the *Magnolia figo* extract is one or more selected from α-cubebene, α-copaene, β-cubebene, β-elemene, β-caryophyllene, γ-elemene, α-humulene, germacrene D, β-selinene, α-selinene, δ-cadinene, germacrene B, and β-caryophyllene oxide.

In the embodiment of the present invention, the use of *Magnolia figo* extract in the manufacture of the compound for inhibiting growth of lung cancer cells is provided, wherein the sesquiterpenol contained in the *Magnolia figo* extract is nerolidol.

In the embodiment of the present invention, the use of *Magnolia figo* extract in the manufacture of the compound for inhibiting growth of lung cancer cells is provided, wherein the monoterpenol contained in the *Magnolia figo* extract is linalool.

In the embodiment of the present invention, the use of *Magnolia figo* extract in the manufacture of the compound for inhibiting growth of lung cancer cells is provided, wherein the ester contained in the *Magnolia figo* extract is methyl(Z)-5,11,14,17-eicosatetraenoate.

As shown in FIGS. 1a to 3c, in the embodiment of the present invention, the use of *Magnolia figo* extract in the manufacture of the compound for inhibiting growth of lung cancer cells is provided, wherein the compound is for facilitating apoptosis of the lung cancer cells.

In detail, the present invention uses the following related manufactured materials and assays to explore the impact of the compound of the present invention on mitochondrial cell apoptosis dependence.

Cell Culture:

In the embodiment of the use of *Magnolia figo* extract in the manufacture of the compound for inhibiting growth of lung cancer cells of the present invention, the present invention uses human non-small cell lung cancer cell line (referred to as "A549 cells") to perform assays. The A549 cells are cultured in DMEM (Dulbecco's modified Eagle's medium) medium containing 10% fetal bovine serum and 1% antibiotics, and grown in an incubator at 37° C. and 5% $CO_2$. When the cells grow to reach 80% of the area of the medium, the present invention proceeds to perform the various assays.

Mtt Assay:

MTT assay is an assay for assessing cell viability rate. In the embodiment of the use of *Magnolia figo* extract in the manufacture of the compound for inhibiting growth of lung cancer cells of the present invention, it observes the impact at different concentrations (1, 2, 5, 10, and 20 µg/ml) of the *Magnolia figo* essential oil extract (also referred to as the flower of *Magnolia figo* "FMO") of the *Magnolia figo* extract on the cell viability rate of the A549 cells by performing the MTT assay.

The A549 cells are cultured in a 96-well plate and placed in an incubator at 37° C., 5% $CO_2$ for 24 hours to allow the cells to attach to the bottom of the plate. After adding different doses of FMO, they are left for 24 and 48 hours respectively. After that, each well of the 96-well plate is added with MTT reagent (0.5 mg/ml), the waste solution is taken out after 4 hours in the dark. Then, each well of the 96-well plate is added with 100 µl of isopropanol, and enzyme-linked immunosorbent assay (ELISA) is performed to measure the absorbance at a wavelength of 562 nm. According to the formula (the experimental group/the control group×100%), the cell viability rates after 24 and 48 hours are calculated respectively, wherein the result of the DMSO group is the result of the control group with DMSO (dimethyl sulfoxide) but without FMO.

Figure 1B:
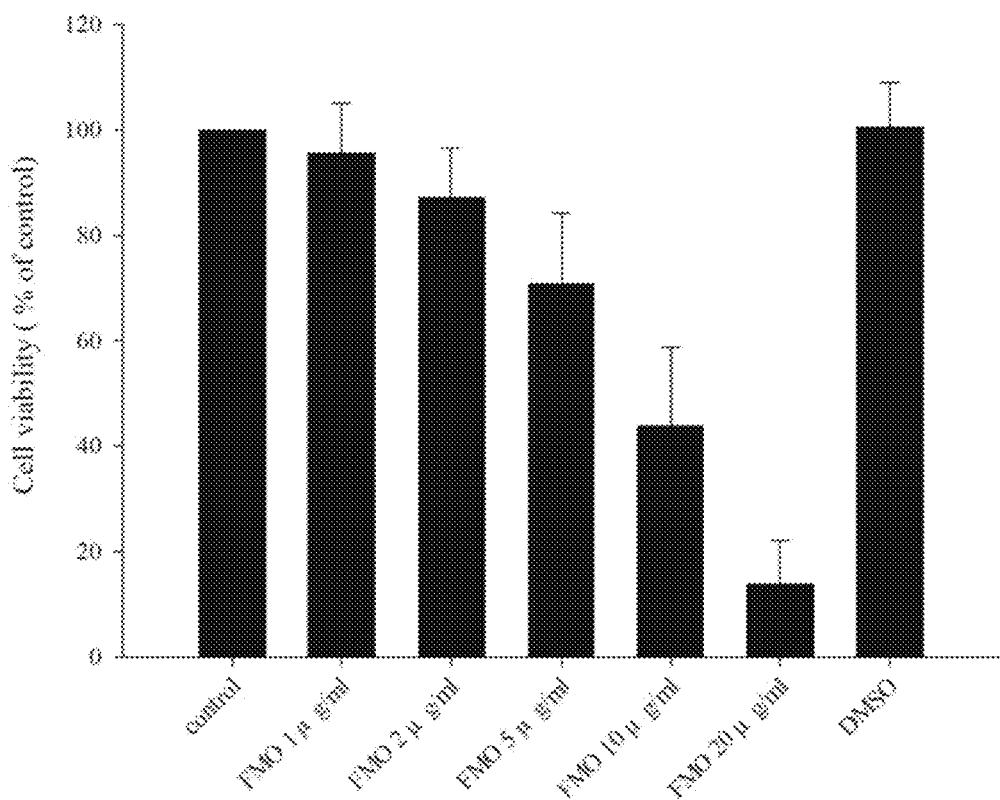
FIG. 1B is a drawing illustrating a bar chart from MTT assay according to the embodiment of the present invention.

As shown in FIGS. 1a to 1b, the MTT assay is performed with the A549 cells, and results of the 24-hour MTT assay are obtained. The half-maximal inhibitory concentration ($IC_{50}$) can be found at FMO 10 µg/ml to 20 µg/ml, wherein the $IC_{50}$ is 8.4±2.8 µg/ml.

Figure 2A:
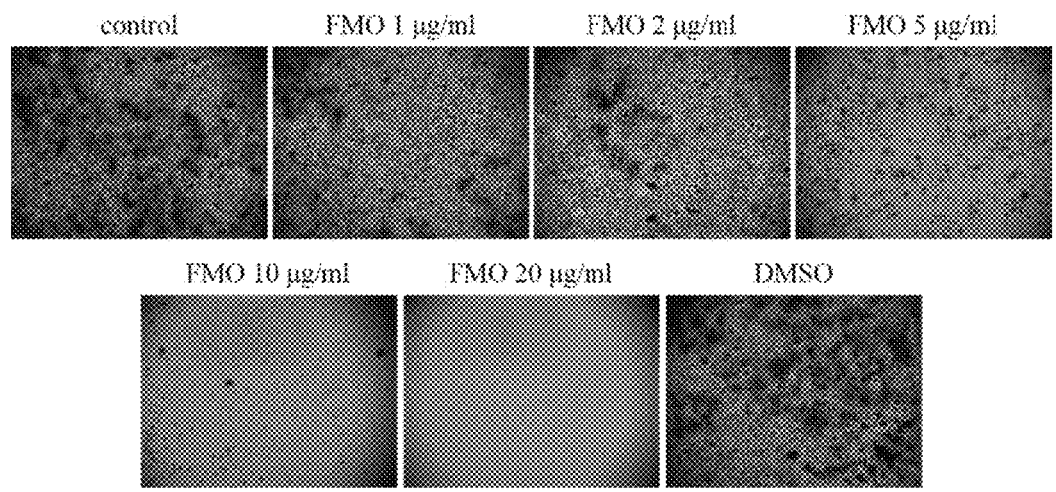
FIG. 2*a* is a drawing showing cell images from MTT assay according to the embodiment of the present invention.
Figure 2B:
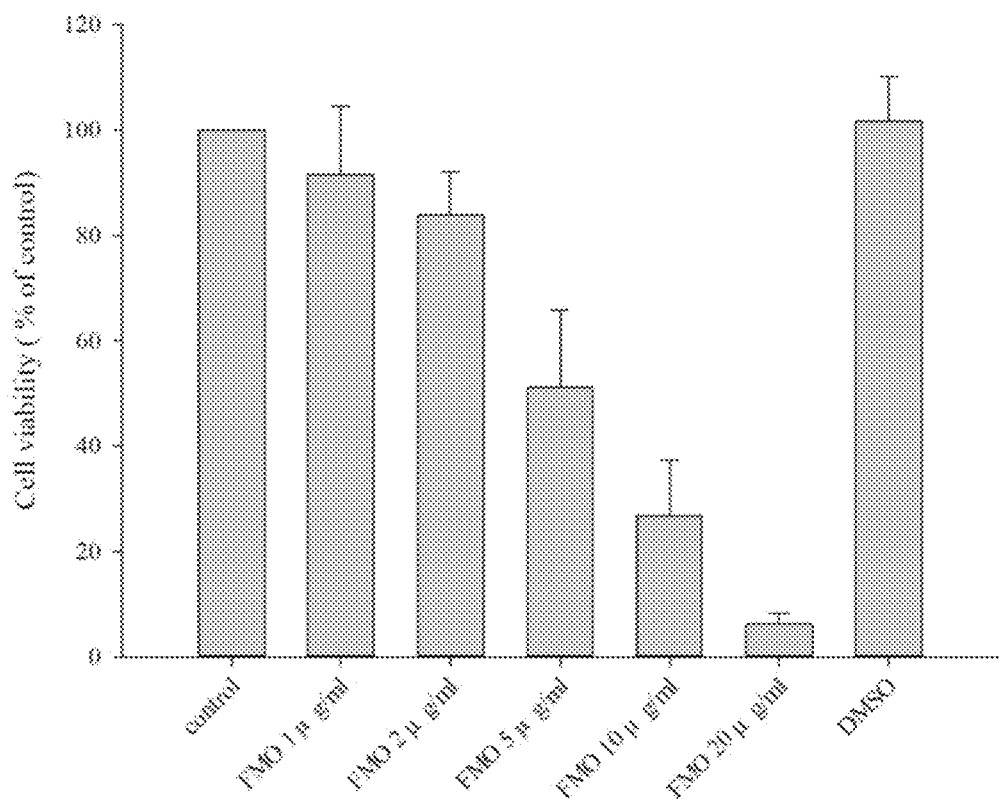
FIG. 2*b* is a drawing illustrating a bar chart from MTT assay according to the embodiment of the present invention.

As shown in FIGS. 2a to 2b, the MTT assay is performed with the A549 cells, and results of the 48-hour MTT assay are obtained. The half-maximal inhibitory concentration ($IC_{50}$) can be found at FMO 5 µg/ml to 10 µg/ml, wherein the $IC_{50}$ is 5.1±1.3 µg/ml.

An analysis of variance (ANOVA) is performed on the aforementioned experimental data by SPSS, and Scheffe's multiple range test is used to test the effect of significant differences of different treatment times.

In detail, as shown in FIGS. 1a to 2b, the cell viability rate of the A549 cells decreases with the increase of the added FMO concentration, thereby showing that the compound of the present invention has an inhibitory effect on lung cancer cells.

Western Blot:

In the embodiment of the use of *Magnolia figo* extract in the manufacture of the compound for inhibiting growth of lung cancer cells of the present invention, the present invention analyzes the expression of related proteins during the apoptosis of the A549 cells by western blot.

In detail, the embodiment of the present invention is based on the western blot to observe the expression level of some proteins related to the apoptosis during the A549 undergoing the apoptosis by adding different concentrations (1, 5, and 10 μg/ml) of FMO to the A549 cells to allow the cells to react. The observed proteins are p53 (tumor suppressor protein), Bax (pro-apoptotic protein), and $Bcl_2$ (anti-apoptotic protein), wherein actin is the control group.

The A549 cells are squamous and narrow and long in the lung tissue, which are responsible for the diffusion of water and electrolytes across alveoli. The A549 cells are also able to synthesize lecithin containing high levels of unsaturated fatty acids by undergoing the citicoline pathway. When the A549 cells are cultured in vitro, they grow as a monolayer adhering or attaching to the culture flask. When the A549 cells are grown for a sufficiently long time in cell culture, A549 cells may begin to differentiate and proliferate. Currently, the A549 cells have been used as a model for studying lung cancer and developing other drug therapies and have served as models of alveolar Type II pulmonary epithelium, finding utility in research examining the metabolic processing of lung tissue and possible mechanisms of drug delivery to the tissue.

Figure 4:
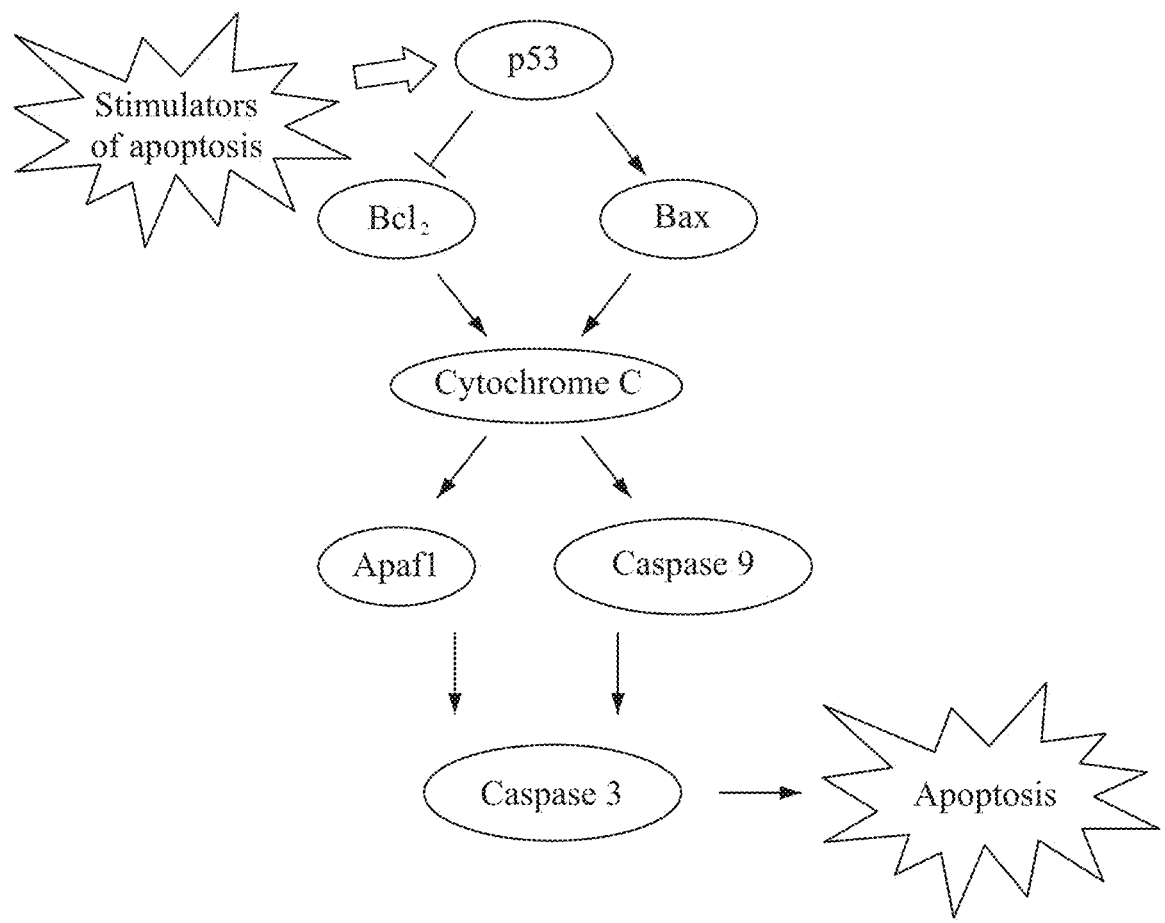
FIG. 4 is a schematic drawing illustrating an apoptosis process according to the embodiment of the present invention.

$Bcl_2$ family proteins can regulate the integrity of mitochondria and are classified as pro-apoptotic and anti-apoptotic proteins, which are mainly found on the mitochondrial membrane, while members of the pro-apoptotic proteins (such as Bax) are usually found in the cytoplasm. As shown in FIG. 4, p53 inhibits $Bcl_2$ and activates Bax. When Bax receives the apoptosis signal, it returns to the mitochondrial surface and forms a hole on the mitochondrial membrane on the surface of the mitochondria, causing a decrease in membrane potential and an increase in membrane permeability, thereby releasing apoptotic factors, such as, cytochrome c. When the cytochrome c is released into the cell, it activates caspase 9 and initiates the cascade reaction of caspase 3, resulting in apoptosis. On the other hand, when the cytochrome c is released into the cell, it may also create an apoptosome by binding with Apaf1 and pro-caspase 9, which then activates the casepase 9 and initiates the cascade reaction of the caspase 3, thereby resulting in apoptosis.

After the A549 cells reacted with lysis buffer, the cell supernatant is obtained, and the protein content is analyzed with protein analysis reagents. After the protein content is analyzed, the appropriate concentration of protein is boiled for 5 minutes to denature the protein. According to experimental requirements, separating gel is prepared, and after the separating gel has solidified, the stacking gel is prepared. An electrophoresis cell is poured with running buffer, each well of the electrophoresis cell is added with an appropriate amount of protein samples, and electrophoresis is performed to separate the proteins. After the above processes are completed, the gel which has run the electrophoresis is placed on a filter paper which has been moistened with 1×transfer buffer, a polyvinyllidene fluoride (PVDF) transfer membrane which has been soaked in methanol is placed on the gel, the wet filter paper is covered on top of the PVDF membrane, and then they are put together and fixed by a fixing clip. After that, they are placed in an electrophoretic transfer cell, and a transfer step at 4° C. is performed thereto. After the transfer is completed, the PVDF membrane is washed with PBST buffer for 15 minutes, then the PVDF membrane is soaked in phosphate-buffered saline (PBS) buffer containing 3% bovine serum albumin (BSA), and the non-specific binding on the PVDF membrane is blocked at room temperature.

Next, the PVDF membrane is infiltrated in the PBST buffer containing 3% BSA and an appropriate of antibodies, which is shaken gently overnight at 4° C., the PVDF membrane is washed 3 times with the PBST buffer the next day, 10 minutes each time, then the moisture on the PVDF membrane is absorbed, a ECL detection kit is added to the PVDF membrane, and the PVDF membrane is sealed in a plastic box. Finally, a luminescence imaging analysis system is used for imaging.

Figure 3A:
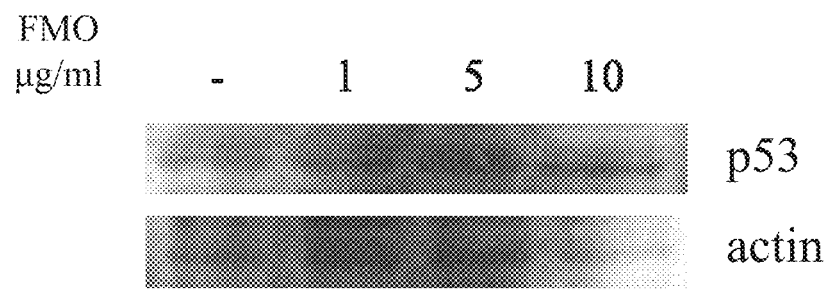
FIG. 3*a* is a drawing showing a protein expression image from the western blot according to the embodiment of the present invention.
Figure 3B:
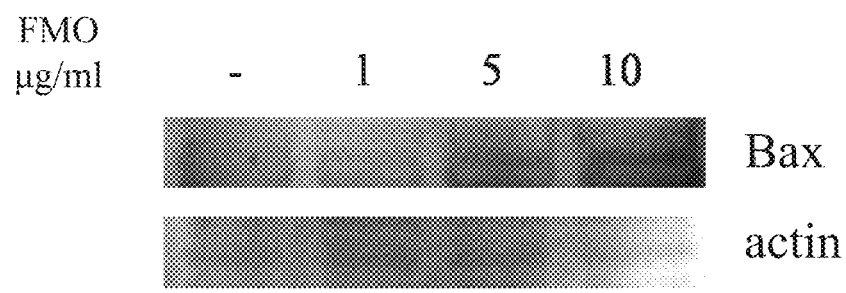
FIG. 3*b* is a drawing showing a protein expression image from the western blot according to the embodiment of the present invention.

As shown in FIGS. 3a to 3b, the expression levels of p53 and Bax in the A549 cells added with 1, 5, and 10 μg/ml FMO are compared to the expression levels of p53 and Bax in the A549 cells without FMO, and the expression levels of p53 and Bax added with 1, 5, and 10 μg/ml FMO increased with the increase of FMO dose.

Figure 3C:
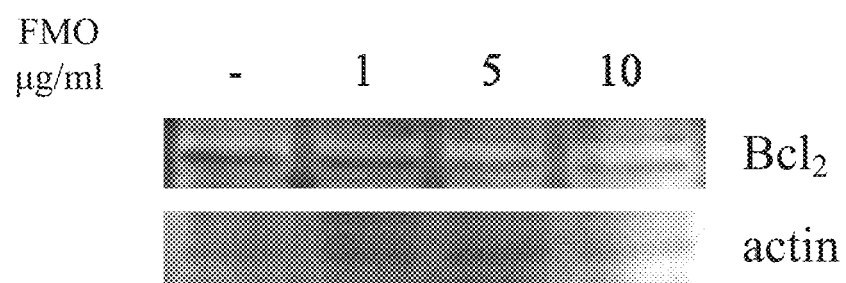
FIG. 3*c* is a drawing showing a protein expression image from the western blot according to the embodiment of the present invention.

As shown in FIG. 3c, the expression level of $Bcl_2$ in the A549 cells added with 1, 5, and 10 μg/ml FMO are compared to the expression level of $Bcl_2$ in the A549 cells without FMO, and the expression level of $Bcl_2$ added with 1, 5, and 10 μg/ml FMO decreased with the increase of FMO dose.

In detail, as shown in FIGS. 3a to 3c, the results obtained by the analysis of the western blot in the embodiment of the present invention show that as the dose of FMO increases, the expression levels of p53 and Bax increase while the expression level of $Bcl_2$ decreases. Based on the results of the above assays, the compound of the present invention has the effect of facilitating apoptosis of the lung cancer cells and thereby inhibiting the growth thereof.

By the technical means adopted by the use of *Magnolia figo* extract in the manufacture of the compound for inhibiting growth of lung cancer cells of the present invention, the present invention can achieve the objective of inhibiting, in a purely natural manner, growth of lung cancer cells. In addition, the present invention can further reduce the physiological and economic burden of patients with lung cancer and save medical costs.

The above description should be considered as only the discussion of the preferred embodiments of the present invention. However, a person having ordinary skill in the art may make various modifications without deviating from the present invention. Those modifications still fall within the scope of the present invention.

What is claimed is:

1. A method for inhibiting growth of lung cancer cells, said method comprises applying a *Magnolia figo* extract to the lung cancer.

2. The method as claimed in claim 1, wherein the *Magnolia figo* extract induces apoptosis of the lung cancer cells.

3. The method as claimed in claim 1, wherein applying the *Magnolia figo* extract comprises applying a *Magnolia figo* essential oil extract having a concentration of 1 to 20 μg/ml in a carrier.

4. The method as claimed in claim 3, wherein the *Magnolia figo* essential oil extract is prepared by the following steps:
   a pre-treatment step of washing and breaking *Magnolia figo*; and
   an extraction step of performing a supercritical fluid extraction on a product obtained in the pre-treatment step to obtain the *Magnolia figo* essential oil extract.

5. The method as claimed in claim 1, wherein applying the *Magnolia figo* extract comprises applying the *Magnolia figo* extract together with an excipient.

6. The method as claimed in claim 1, wherein the *Magnolia figo* extract comprises sesquiterpene, sesquiterpenol, monoterpenol, and ester.

7. The method as claimed in claim 6, wherein the sesquiterpene is one or more selected from α-cubebene, α-copaene, β-cubebene, β-elemene, β-caryophyllene, γ-elemene, α-humulene, germacrene D, β-selinene, α-selinene, δ-cadinene, germacrene B, and β-caryophyllene oxide.

8. The method as claimed in claim 6, wherein the sesquiterpenol comprises nerolidol.

9. The method as claimed in claim 6, wherein the monoterpenol comprises linalool.

10. The method as claimed in claim 6, wherein the ester is methyl(Z)-5,11,14,17-eicosatetraenoate.

* * * * *